United States Patent
Biagtan et al.

[11] Patent Number: 6,146,339
[45] Date of Patent: Nov. 14, 2000

[54] GUIDE WIRE WITH OPERATOR CONTROLLABLE TIP STIFFNESS

[75] Inventors: Emmanuel Biagtan, Temecula; David M. Anderson, Oceanside, both of Calif.

[73] Assignee: Advanced Cardiovascular Systems, Santa Clara, Calif.

[21] Appl. No.: 09/317,574

[22] Filed: May 24, 1999

[51] Int. Cl.$^7$ ...................................................... A61B 5/00
[52] U.S. Cl. ................ 600/585; 604/95; 604/96
[58] Field of Search .................... 600/585, 433, 600/434; 604/95, 96, 280, 281, 282

[56] References Cited

U.S. PATENT DOCUMENTS

| | | |
|---|---|---|
| Re. 33,911 | 5/1992 | Smason et al. . |
| Re. 34,466 | 12/1993 | Taylor et al. . |
| Re. 34,695 | 8/1994 | Mar et al. . |
| 4,215,703 | 8/1980 | Wilson . |
| 4,468,224 | 8/1984 | Enzmann et al. . |
| 4,538,622 | 9/1985 | Samson et al. . |
| 4,554,929 | 11/1985 | Samson et al. . |
| 4,601,705 | 7/1986 | McCoy . |
| 4,619,274 | 10/1986 | Morrison . |
| 4,716,757 | 1/1988 | McGregor et al. . |
| 4,721,117 | 1/1988 | Mar et al. . |
| 4,748,986 | 6/1988 | Morrison et al. . |
| 4,827,941 | 5/1989 | Taylor et al. . |
| 4,838,859 | 6/1989 | Strassmann . |
| 4,846,193 | 7/1989 | Tremulis et al. . |
| 4,867,174 | 9/1989 | Skribiski . |
| 4,875,489 | 10/1989 | Messner et al. . |
| 4,907,332 | 3/1990 | Christain et al. . |
| 4,917,102 | 4/1990 | Miller et al. . |
| 4,932,959 | 6/1990 | Horzewski et al. . |
| 4,940,062 | 7/1990 | Hampton et al. . |
| 4,953,553 | 9/1990 | Tremulis . |
| 4,955,384 | 9/1990 | Taylor et al. . |
| 4,964,409 | 10/1990 | Tremulis . |
| 4,966,163 | 10/1990 | Kraus et al. . |
| 4,984,581 | 1/1991 | Stice . |
| 4,998,916 | 3/1991 | Hammerslag et al. . |
| 5,007,434 | 4/1991 | Doyle et al. . |
| 5,055,101 | 10/1991 | McCoy . |
| 5,055,109 | 10/1991 | Gould et al. . |
| 5,090,956 | 2/1992 | McCoy . |
| 5,092,901 | 3/1992 | Hunter et al. . |
| 5,135,503 | 8/1992 | Abrams et al. . |
| 5,143,085 | 9/1992 | Wilson . |
| 5,271,415 | 12/1993 | Foerster et al. . |
| 5,282,478 | 2/1994 | Fleischhaker, Jr. et al. . |
| 5,303,714 | 4/1994 | Abele et al. . |
| 5,341,818 | 8/1994 | Abrams et al. . |
| 5,346,945 | 9/1994 | Hodgson et al. . |
| 5,349,964 | 9/1994 | Imran et al. . |
| 5,364,355 | 11/1994 | Alden et al. . |
| 5,388,590 | 2/1995 | Horrigan et al. ........................ 600/585 |
| 5,411,476 | 5/1995 | Abrams et al. . |
| 5,415,633 | 5/1995 | Lazarus et al. . |
| 5,427,118 | 6/1995 | Nita et al. . |
| 5,437,288 | 8/1995 | Schwartz et al. ........................ 600/585 |
| 5,447,503 | 9/1995 | Miller . |
| 5,480,382 | 1/1996 | Hammerslag et al. . |

(List continued on next page.)

*Primary Examiner*—Cary O'Connor
*Assistant Examiner*—Pamela L. Wingood
*Attorney, Agent, or Firm*—Blakely, Sokoloff, Taylor & Zafman, LLP

[57] ABSTRACT

An improved method and apparatus for providing a readily insertable guide wire that is also accurately steerable. One embodiment of the present invention comprises one or more thin diameter, liquid filled, polymer balloons enclosed by the guide wire coils and connected through a hypotube lumen to a pressure transducer. The pressure transducer exerts pressure via a fluid medium to the balloon(s), which then expand and exert pressure onto the inner surface of the coils, thereby stiffening the distal section of the guide wire. In operation, the guide wire will typically be inserted with the balloons deflated, hence the distal tip is very flexible. Once the distal tip reaches its destination, the balloons are inflated and expanded to stiffen and/or reorient the distal tip to allow it to perform as required, typically by aiding in the positioning of a catheter or stent in the desired location.

46 Claims, 12 Drawing Sheets

U.S. PATENT DOCUMENTS

| | | |
|---|---|---|
| 5,507,301 | 4/1996 | Wasicek et al. . |
| 5,542,434 | 8/1996 | Imra et al. . |
| 5,558,101 | 9/1996 | Brooks et al. . |
| 5,571,094 | 11/1996 | Sirhan . |
| 5,605,162 | 2/1997 | Mirzaee et al. . |
| 5,636,641 | 6/1997 | Fariabi . |
| 5,637,089 | 6/1997 | Abrams et al. . |
| 5,643,209 | 7/1997 | Fugoso et al. . |
| 5,695,111 | 12/1997 | Nanis et al. . |
| 5,697,380 | 12/1997 | Quiachon et al. . |
| 5,749,370 | 5/1998 | Brooks et al. . |
| 5,762,615 | 6/1998 | Weier . |
| 5,769,819 | 6/1998 | Schwab et al. . |
| 5,813,997 | 9/1998 | Imran et al. . |
| 5,827,225 | 10/1998 | Ma Schwab . |

GUIDE WIRE WITH OPERATOR CONTROLLABLE TIP STIFFNESS

BACKGROUND OF THE INVENTION

1. Field of the Invention

The present invention relates to guide wires used in medical procedures to gain access to specific areas of the body without major surgery. More specifically, the present invention deals with a flexible guide wire having a controllable stiffness.

2. Description of Related Art

Medical catheters generally comprise elongate tube-like members that may be inserted into the body, either percutaneously or via a body orifice, for any of a wide variety of diagnostic and interventional purposes. Such catheters are particularly useful with regard to certain cardiovascular applications where the object is to deliver a treatment or instrument to a remote lesion. Often, the instrument must cross a lesion consisting of hard and inflexible tissue having a very rough surface or even protruding flaps. For example, Percutaneous Transluminal Coronary Angioplasty (PTCA or balloon angioplasty) requires manipulation of a catheter through extended portions of the patient's arterial system to the stenotic site for the purposes of alleviating the lesion by inflating a balloon.

A PTCA guide wire is typically a long, flexible wire, coiled or uncoiled, having one or more components. The guide wire is generally used to gain access to a body structure or location by inserting it transluminally into the brachial or femoral artery and then advancing it to the desired location. The guide wire can be used to probe, biopsy, penetrate, dilate, or act as a vehicle for transporting an accompanying catheter to a given location. PTCA procedures generally require a guide wire flexible enough to go around bends and yet stiff enough to be pushable and capable of driving through the arterial blockage. Thus, the goal in designing a guide wire is to design a flexible and directable guide wire still capable of pushing through blockage at the stenotic site.

Coronary arteries, however, are circuitous and/or tortuous and have many sub-branches. Often, the stenotic region is located where the diameter of the artery is small, or, by its very presence, the stenotic region leaves only a very small opening through which a guide wire can pass. Effective steering of the tip and/or body of the guide wire becomes very important for the quick, safe, and accurate passage and placement of the guide wire preceding the transport and positioning of a PTCA catheter. Thus, guide wires have often been provided with flexible distal tips. The flexible tip allows the cardiologist to pre-bend the distal tip of the guide wire before insertion and then rotate (or torque) the guide wire once it has reached a branch artery to enable the bent tip to enter the branch. Typically, the very distal 1 cm. of the guide wire is bent into a J-shape of approximately 5–10 mm. Note that a cardiologist is not limited to a J-shape and may choose any shape that will be helpful in directing the guide wire to negotiate turns.

The cardiologist encounters several difficulties in attempting to rotate the prebent guide wire into the desired position. For example, particular difficulty is met with pre-bending in cases where an artery branches at a first angle and then sub-branches at a second angle. As a result, if the cardiologist is unable to enter the desired arterial branch through rotation of the guide wire, the pre-bent tip may need to be adjusted. If adjustment is required, the guide wire is removed, re-bent, and reinserted, often multiple times during a single procedure. With repeated removal and reinsertion of the guide wire, the procedure is accompanied by the risk of significant trauma to the arterial lining, and in many cases, the obstruction cannot be reached at all. The necessity of repeatedly removing and adjusting the guide wire also increases the time and cost associated with each procedure. Further, rotation of the distal end of the guide wire typically lags behind rotation of the proximal end of the wire (i.e., the control end), such that precise rotational control by the cardiologist is difficult, if at all possible. Friction in the arteries can cause the distal end to rotate in a jerky fashion, rather than a slow consistent motion, which can traumatize the vascular intima and also interfere with the rotational control. Any one or combination of these issues may prevent the cardiologist from successfully directing the guide wire into the desired arterial branch.

In an effort to address the above difficulties, guide wires have often been provided with a stiffer distal extremity (tip) in order to achieve the stiffness required to place a stent in the desired location. However, when such a guide wire employs a stiff distal tip, it is difficult for the guide wire to initially enter the vessel and negotiate tortuous sites encountered in the vessel. Thus, it is generally preferred for the tips of guide wires to be floppy at entry. These conflicting yet essential characteristics of a functional guide wire have often made it necessary to utilize two separate guide wires in a single procedure. A guide wire having a floppy distal extremity for directing the wire into the desired location through the arterial branches is inserted first. The floppy guide wire is then replaced by a second guide wire having a stiffer distal tip for actually positioning the catheter in the desired location.

A variety of constructions have been proposed to provide guide wires steerable from the proximal end that still allow the guide wire to be advanced through non-linear cavities without removal for adjustments or the use of a separate additional guide wire. These constructions include shape memory alloy devices that when heated change orientation, and devices employing wires or pulleys to steer the tip from a handle located outside the body. However, each of these devices has significant limitations.

Shape memory alloy devices are devices whose shape changes as the device is heated or cooled. For example, a device may initially have a small J-shape, but when heated develops a larger more defined J-shape. The heating of a shape memory alloy device may be provided by a change in body temperature (i.e., the guide wire is inserted further into the body) or through resistance heating. When using resistance heating, the guide wire core contains one or more wires through which a current is supplied to the tip of the guide wire. Actuators are coupled to the wire(s) to supply the current, and multiple actuators can be used to further vary the movement or developing shape of the guide wire's distal tip. However, such devices are very expensive, and typical guide wire constraints allow limited space for the actuating element(s). Not only do shape memory alloy devices possess cost and size restraints, they also often have a slow response time due to their reliance on heat transfer as the operative control mechanism.

Guide wires using pulley systems have been developed having filaments that run through the core of the guide wire. The filaments are manipulated, often through use of a joystick, to control the orientation of the distal tip. Such devices have problems achieving control over long distances, since long small diameter wires requiring only minimal changes in length to actuate do not afford very precise control. In addition, the cable tension required for such devices to work effectively dictates that the stiffness of the tip, which is critical to device effectiveness, be altered by an actuating mechanism. The overall size of the device trades off against the ability to tension the cable, where the strain in the tensioned cable increases as device size decreases.

In addition to limited steerability, both types of prior art guide wires rely on the spring tension of the guide wire coil to return the guide wire to a straight, unbent position. However, straightening the wire after negotiating the branch is as important as deflecting the wire for entry into a branch artery. Any ability to straighten prior art devices described above is from spring tension or other structures in the distal end of the wire, both of which serve to compromise the desired floppiness of the guide wire tip.

Thus, it is desirable to provide a readily insertable guide wire that is also accurately steerable. Effective control over tip or body deflection and stiffness of the wire, which provides the necessary steering capability, is important so that the guide wire can be quickly and accurately steered and guided through a desired path to the desired location within the body. It is desirable to achieve a remotely steerable catheterization device that does not incur the penalties of stiffness, precision, or size currently associated with the prior art devices.

SUMMARY OF THE INVENTION

An improved method and apparatus for providing a readily insertable guide wire that is also accurately steerable is described. One embodiment of the present invention comprises one or more thin diameter, liquid filled, polymer balloons running substantially parallel to the guide wire core, both of which are enclosed by coils and connected through a lumen to a pressure transducer. The pressure transducer exerts pressure via a fluid medium to the balloon (s) which then expand and exert pressure onto the inner surface of the coils, thereby stiffening the length and distal section of the guide wire. In operation, the guide wire will typically be inserted with the balloons deflated, hence the distal tip is very flexible (i.e., floppy, easily directed). Once the distal tip reaches its destination, the balloons may be inflated and expanded to stiffen and/or reorient the distal tip of the guide wire and allow it to perform as required, typically by aiding in the positioning of a catheter or stent in the desired location.

BRIEF DESCRIPTION OF THE DRAWINGS

The invention is further described by way of example with reference to the accompanying drawings, wherein:

FIG. 11B-1 is a side cross-sectional view of a first configuration of the guide wire illustrated in FIG. 11A.

FIG. 11B-2 is a side cross-sectional view of a second configuration of the guide wire illustrated in FIG. 11A.

DETAILED DESCRIPTION OF THE INVENTION

A method and apparatus providing a flexible guide wire having an operator controllable (i.e., variable) stiffness is described. In the following detailed description, numerous specific details are set forth in order to provide a more thorough understanding of the present invention. However, it will be appreciated that the present invention may be practiced without these specific details. In other instances, well-known devices, methods, procedures, and individual components have not been described in detail so as not to unnecessarily obscure aspects of the present invention.

Embodiments of the present invention are described herein in reference to a steerable guide wire for use in percutaneous transluminal coronary angioplasty (PTCA) procedures and/or other vascular intervention procedures. However, it is appreciated that the present invention can be readily adapted for other purposes, such as, but not limited to, balloon and laser angioplasty, nephrostomy, electrode placement, etc. These applications can all benefit from an increased degree of control of the steerability and stiffness of the body and/or tip of the guide wire and/or catheter from a remote site located external to the body.

Tremendous progress has been made in the realm of therapeutic devices. To treat human coronary atherosclerosis, angioplasty balloon catheters, stents, and guide wires are being used at high frequency. Thus, improvements to the biomedical devices that reduce the time, risk, and cost, while improving the success rate of operations involving their use are desirable. The present invention provides such advantages and comprises a guide wire whose distal tip flexibility and shape can be varied and controlled with precision by the operator. In all other regards, however, the present invention performs similarly to conventional guide wires in that it is inserted transluminally into the body and directed to the treatment site, typically to allow for subsequent delivery of a catheter to the desired region.

Figure 1:
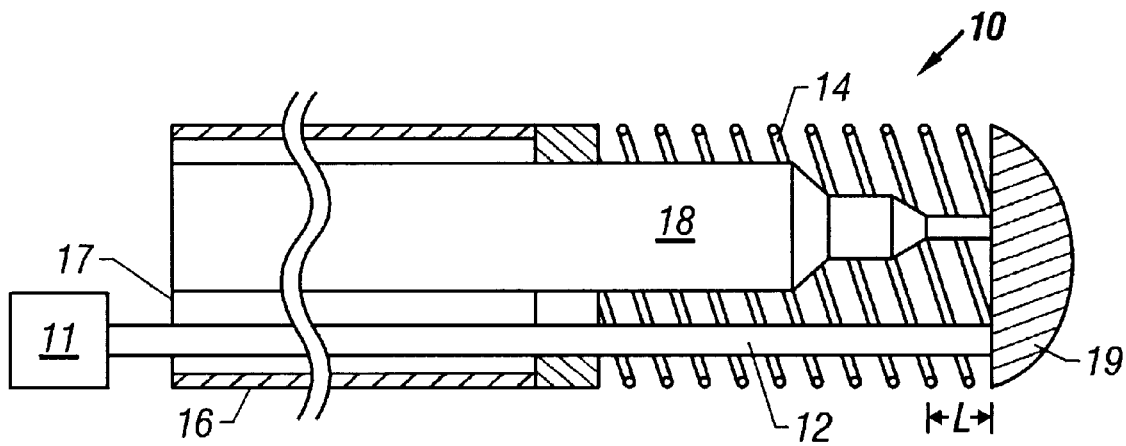
FIG. 1 is a side cross-sectional view of a first embodiment of the present invention.

In brief summary, a first embodiment of the guide wire 10 of the present invention is illustrated in FIG. 1. The first embodiment comprises one or more thin diameter, liquid filled, polymer balloons 12 enclosed by the coils 14. The polymer balloons 12 are disposed substantially parallel to the core 18, and are connected through lumen 17 of support shaft 16 (e.g., a hypotube, a polymer, or a coil) to an inflation device 11 (e.g., a pressure transducer or manual balloon indeflator). Shaft 16 may be a housing having a cylindrical shape or any other shape. In this, or any other embodiment, polymer balloons 12 may also be disposed in any arrangement through lumen 17 (e.g., surrounding core 18, on one side of core 18, circling core 18, etc.) Note that the core 18 does not have to decrease in a linear step motion as shown; other configurations and/or shapes may also be used.

The inflation device 11 exerts pressure via a fluid medium to the balloon(s) 12, which then expand and exert pressure onto the inner surface of the coils 14 and/or core 18, to thereby stiffen both the length (L) of the guide wire 10 and the distal section (tip) 19. The length (L) that is stiffened is typically only the distal 0.5–4.0 cm, which is generally the final grind as the core 18 steps down. In operation, the guide wire 10 will typically be inserted with the balloon(s) 12 deflated, such that guide wire 10 is very flexible, easily directed, and generally bent. The primary purpose of the tip 19 is for steering—taking hard angles, branches, etc. The primary purpose for stiffening the tip 19 is for pushing through lesions, but it can also help navigate turns/branches, most easily by changing the tip stiffness/orientation while negotiating a hard branch.

Once the tip 19 reaches its destination, the balloons 12 are typically inflated and expanded to stiffen and straighten the length (L) and distal end 19 of the guide wire 10. Alternatively, the balloon(s) may be inserted partially or wholly inflated and deflated/inflated at appropriate times to maneuver as needed. The balloon(s) 12 may be prefabricated such that they assume a particular shape once inflated. In this manner, the various embodiments of the present invention provide a guide wire 10 having both a controllable/variable overall stiffness and a controllable/variable shape and/or position/orientation of both the length (L) and the distal end 19.

Figure 2:
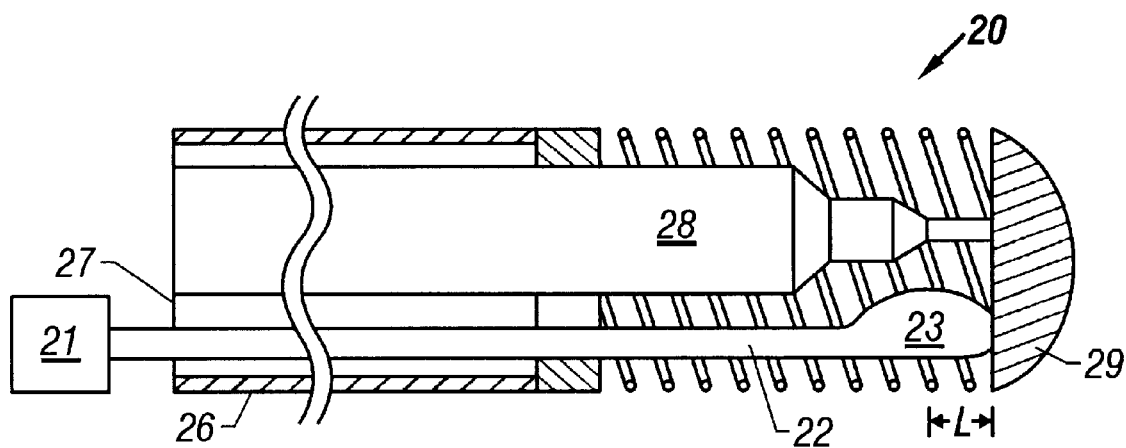
FIG. 2 is a side cross-sectional view of a second embodiment of the present invention.

In a second embodiment illustrated in FIG. 2, a guide wire 20 of the present invention provides a slightly modified version of the guide wire illustrated in FIG. 1. In this second embodiment, the guide wire 20 comprises one or more thin diameter, liquid filled, polymer balloon stems 22 of a first diameter having a balloon 23 of a second and typically larger diameter at the balloon stem's 22 distal end. In one embodiment, the balloon stem 22 has an approximate diameter of 0.001–0.005 in. and an approximate length of 150–300 cm. (almost the same length as the wire). In this embodiment, the balloon 23 is approximately 0.5–4.0 cm. long and has an approximate diameter of 0.001–0.030 in.

The balloon stems 22 run substantially parallel to the core 28 and are connected through lumen 27 of support shaft 26 to an inflation device 21. The inflation device 21 exerts pressure via a fluid medium through the balloon stems 22 to the balloons 23, which both then expand and exert pressure onto the inner surface of the coils 24. In this manner, the balloon stems 22 provide added stiffness to the length (L) of the guide wire 20. Similarly, the balloons 23 provide a stiffness to the distal section 29 of the guide wire 20 in addition to providing a re-orientation of the position of the distal section 29 of the guide wire 20. In operation the guide wire 20 will typically be inserted with the balloon stem 22 and the balloons 23 deflated, hence the guide wire 20 is very flexible and easily directed. Once the tip 29 reaches its destination, balloon stem 22 and balloon 23 are inflated and expanded to stiffen the length (L) and distal end 29 of the guide wire 20. Further, the expanded balloon 23 will also typically exert a pressure at the distal end of the core 28. This added pressure to the distal end of the core 28 will cause a slight to substantial (depending on the size, placement, and inflated pressure of the balloon 23) bending of the distal end/tip 29 of the guide wire 20. Alternatively, the balloon stem 22 and balloon 23 may be deflated, returning he guide wire 20 to a flexible and easily directed state. Thus, the second embodiment of the present invention provides a guide wire 20 having both a controllable/variable overall stiffness and a controllable/variable shape and/or orientation of both the length (L) and distal end section 29 of the guide wire 20.

Figure 3A:
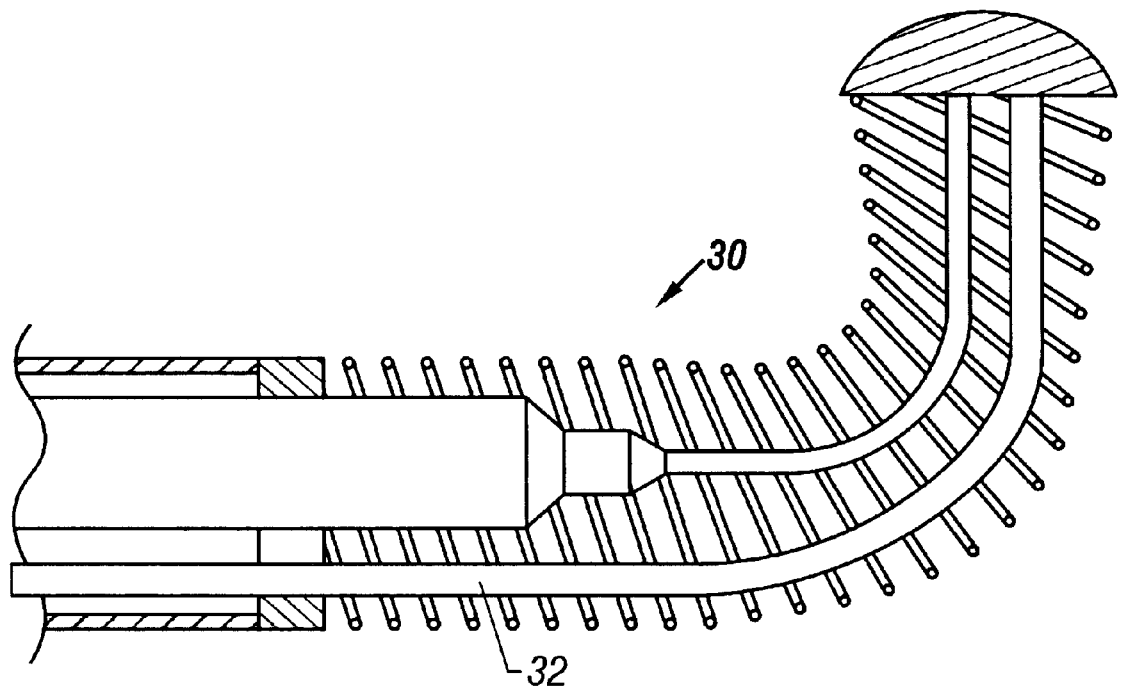
FIG. 3A is a side cross-sectional view of a third embodiment of the present invention wherein the balloon is substantially deflated and the guide wire is flexible and sharply curved.
Figure 3B:
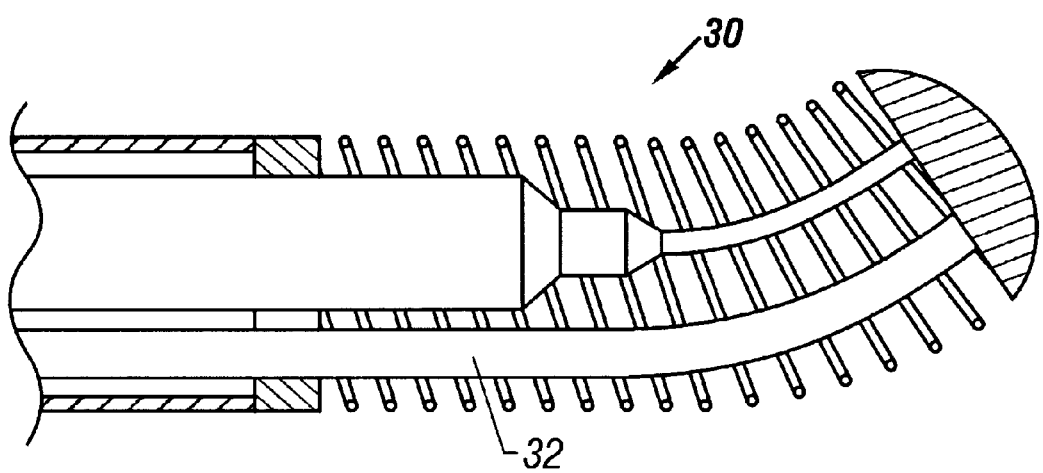
FIG. 3B is a side cross-sectional view of a third embodiment of the present invention wherein the balloon is substantially inflated and the guide wire is stiff and slightly bent.

In a third embodiment, a guide wire 30 of the present invention provides an overly J-shaped wire. FIGS. 3A and 3B illustrate guide wire 30 in both the deflated (i.e., flexible and sharply curved) and inflated (i.e., stiff and slightly bent) positions, respectively. Note that the dimensions of the balloon 32 may increases when inflated or may remain substantially the same with balloon 32 itself simply becoming more rigid. This third embodiment of the present invention would be particularly useful by providing both a normal J-shape (see FIG. 3B) for typical use and an extreme J-shape (See FIG. 3A) for a tortuous path. Note that FIGS. 3A and 3B illustrate a balloon 32 having an approximately constant diameter similar to the narrow balloon 12 illustrated in FIG. 1. However, it is possible to provide a guide wire having an initial J-shape such as the one described in this third embodiment, wherein the balloons 32 are replaced with a balloon stem having an enlarged diameter section at its distal end, similar to the balloon stem 22 and balloon 23 of FIG. 2.

Figure 4A:
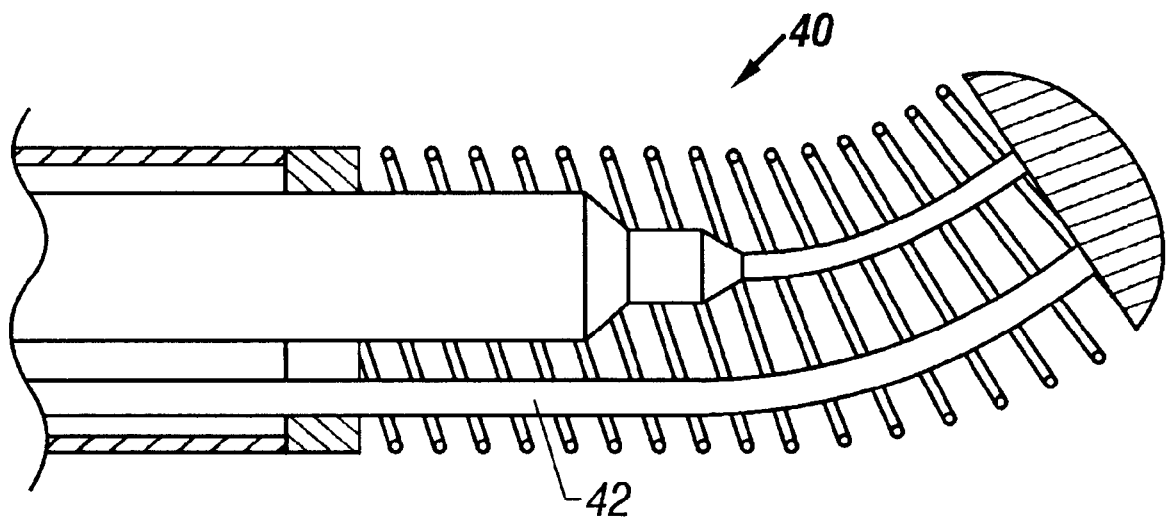
FIG. 4A is a side cross-sectional view of a fourth embodiment of the present invention wherein the balloon is substantially deflated and the guide wire is flexible and partially curved.
Figure 4B:
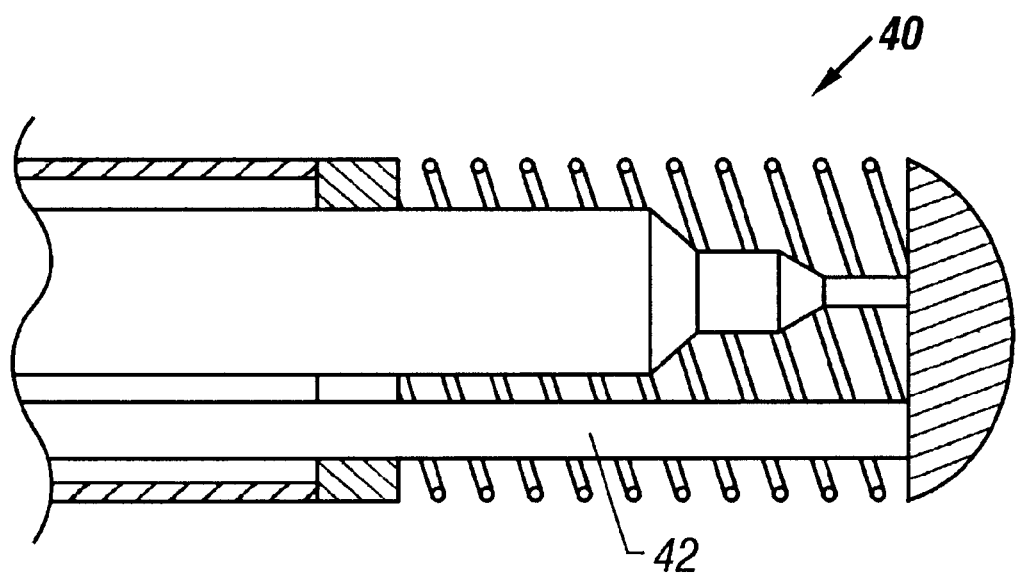
FIG. 4B is a side cross-sectional view of a fourth embodiment of the present invention wherein the balloon is substantially inflated and the guide wire is stiff and relatively straight.

A fourth embodiment provides a guide wire 40 of the present invention very similar to that discussed above with respect to the third embodiment. FIGS. 4A and 4B illustrate a guide wire 40 in both the deflated (i.e., flexible and partially curved) and inflated (i.e., stiff and substantially straight) position, respectively. This fourth embodiment of the present invention provides a normal J-shaped guide wire 40. The balloon 42 of guide wire 40 will typically be deflated for normal use and then subsequently inflated to straighten and stiffen the guide wire for crossing the lesion. Note that as with the third embodiment, the balloon 42 is illustrated as having an approximately constant diameter similar to the balloon 12 shown in FIG. 1. However, it is possible to provide a guide wire 40 wherein the balloon 42 is replaced with a balloon stem having an enlarged diameter section at its distal end, similar to the balloon stem 22 and balloon 23 of FIG. 2.

Figure 5A:
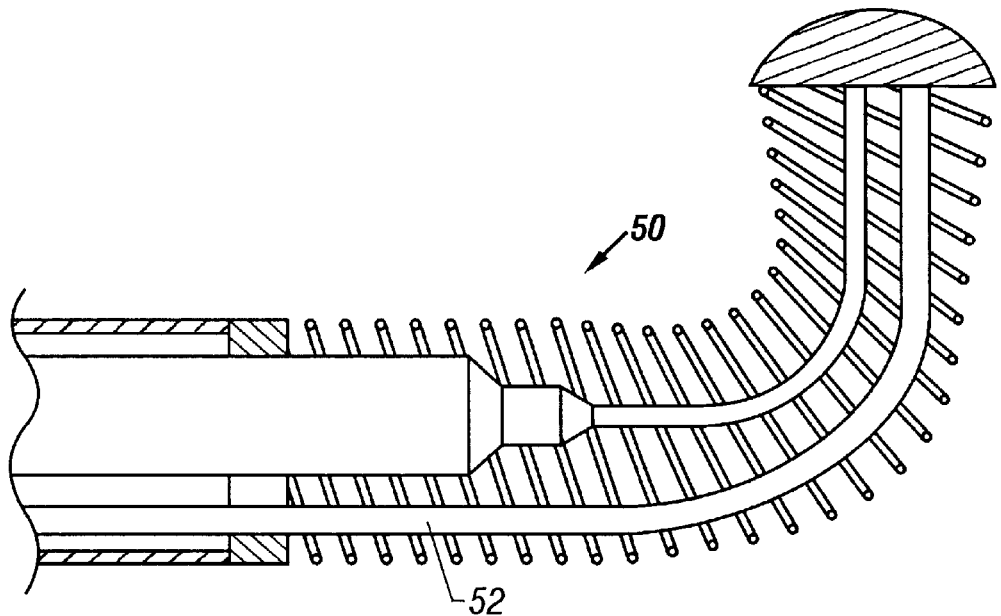
FIG. 5A is a side cross-sectional view of a fifth embodiment of the present invention wherein the balloon is substantially deflated and the guide wire is flexible and sharply curved.
Figure 5B:
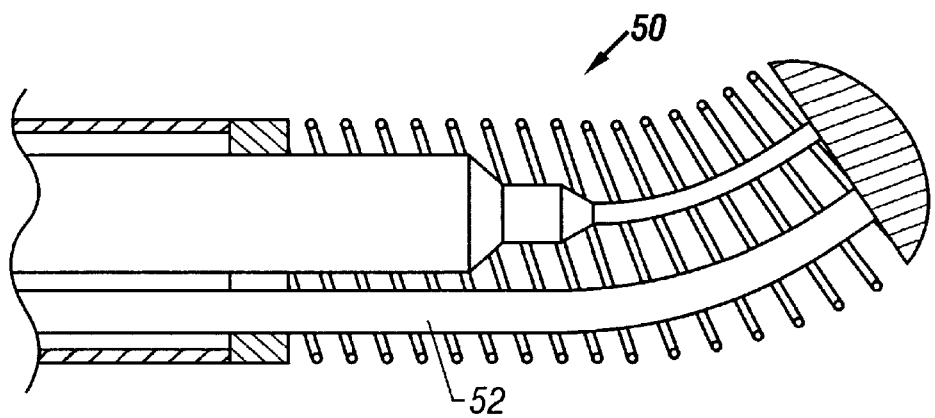
FIG. 5B is a side cross-sectional view of a fifth embodiment of the present invention wherein the balloon is partially inflated and the guide wire is moderately stiff and slightly bent.
Figure 5C:
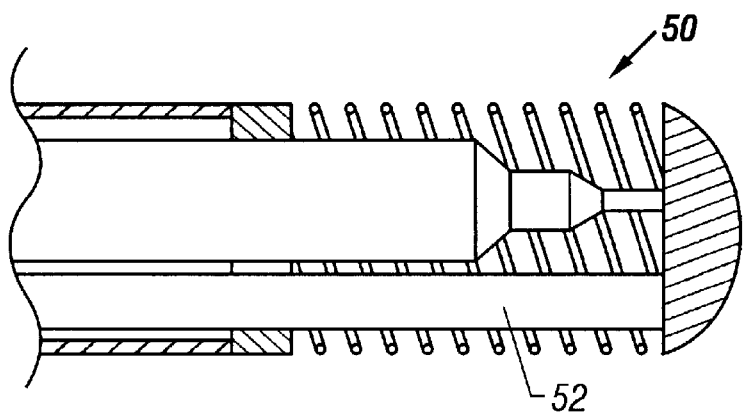
FIG. 5C is a side cross-sectional view of a fifth embodiment of the present invention wherein the balloon is substantially inflated and the guide wire is stiff and relatively straight.

A fifth embodiment of the present invention is generally a combination of the third and fourth embodiments described above. FIGS. 5A, 5B, and 5C illustrate a guide wire 50 having three positions (i.e., orientations or degrees of inflation). A first position having an extreme J-shape is illustrated in FIG. 5A, wherein the balloon 52 of the guide wire 50 is substantially deflated such that the guide wire 50 is both flexible and sharply curved. The sharp curve of deflated guide wire 50 is particularly useful in negotiating tortuous anatomy. A second position having a more normal J-shape is illustrated in FIG. 5B, wherein the balloon 52 of guide wire 20 is partially inflated. For example, the second position of the guide wire 50 is approximately half inflated at a low pressure. This second, partially inflated position provides for a normal J-shape having an increased stiffness over the first position. A third position providing a stiff, relatively straight guide wire 50 is illustrated in FIG. 5O, wherein the balloon 52 of the guide wire 50 is substantially fully inflated at a high pressure such that the guide wire 50 is both relatively straight and stiff. This third, straight, stiff position of guide wire 50 is capable of providing the desired pushability characteristics required for lesion crossing.

Note that as with the third and fourth embodiments, the balloon 52 of the fifth embodiment is illustrated having an approximately constant diameter similar to the balloon 12 shown in FIG. 1. However, it is possible to provide a guide wire 50 wherein the balloon 52 is replaced with a balloon stem having an enlarged diameter section at its distal end similar to the balloon stem 22 and balloon 23 of FIG. 2. Note also that although the fifth embodiment describes a guide wire 50 having three positions, the guide wire is not limited to merely three positions. In fact, by varying the amount of pressure delivered by the pressure transducer to the balloon 52, numerous degrees of flexibility and position/orientation of the guidewire 50 may be achieved.

Each of the five embodiments discussed above provide a general overview of different possibilities for use of the present invention. Variations to the actual guide wire itself may further facilitate use of a balloon to control the flexibility, orientation, and/or position of the guide wire. For example, one embodiment may comprise a lumen (e.g., a hypotube) containing a core member and a balloon stem running through the entire length of the hypotube. An alternative embodiment may be comprised of a lumen having a distal core member attached at the distal end of the lumen and a balloon stem running all the way through (i.e., the entire length) of the lumen. Note also that the lumen of both the above embodiments may be replaced by a ribbon wire (flat profile) coil or a round wire coil under compression and ground flat (i.e., round on the inner diameter and flat on the outer diameter).

Figure 6A:
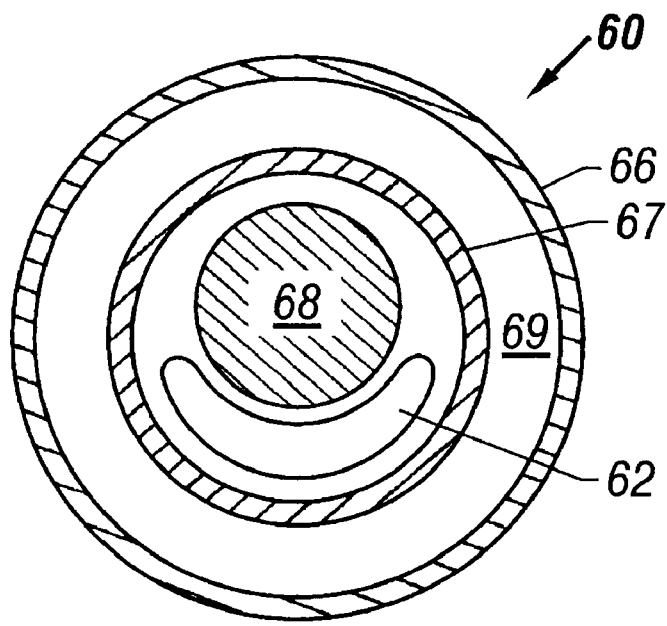
FIG. 6A is a proximal cross-sectional view of an embodiment of the present invention wherein the core and balloon are encompassed by a shrunken polymer tube.
Figure 6B:
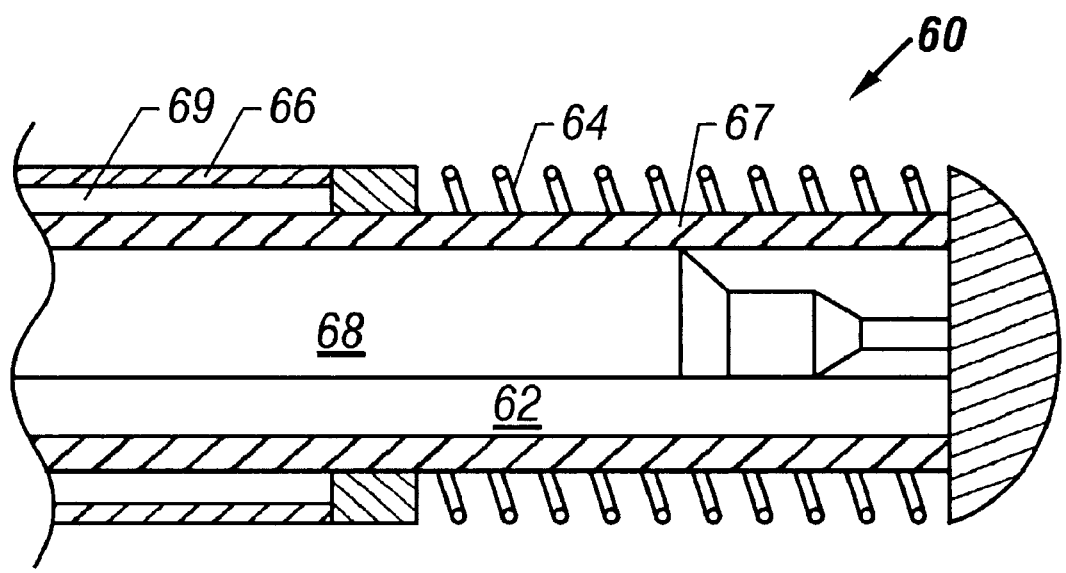
FIG. 6B is a side cross-sectional view of the embodiment of the present invention illustrated in FIG. 6A.

Another alternative to the fabrication of a guide wire of the present invention is illustrated in FIGS. 6A and 6B. In FIGS. 6A and 6B, the guide wire 60 is comprised of a single core member 68 and balloon stem 62 running through the entire length of the lumen 69 of support shaft 66. The core 68 and balloon stem 62 are then covered by a shrunken polymer tube 67 over the proximal portion. In this embodiment, the balloon stem 62 can be either substantially rigid (i.e., hold a substantially defined cross-sectional shape) or substantially flexible (i.e., substantially conform to the shape of the core member 68) to best conform within the tube 67. FIGS. 6A and 6B illustrate a flexible balloon stem 62 conforming around the core 68 once within the shrunken polymer jacket 67. For one embodiment, shaft 66 and/or coils 64 are not required. In a second embodiment, shaft 66 extends over the tip coils 64, covering the complete wire.

Figure 7A:
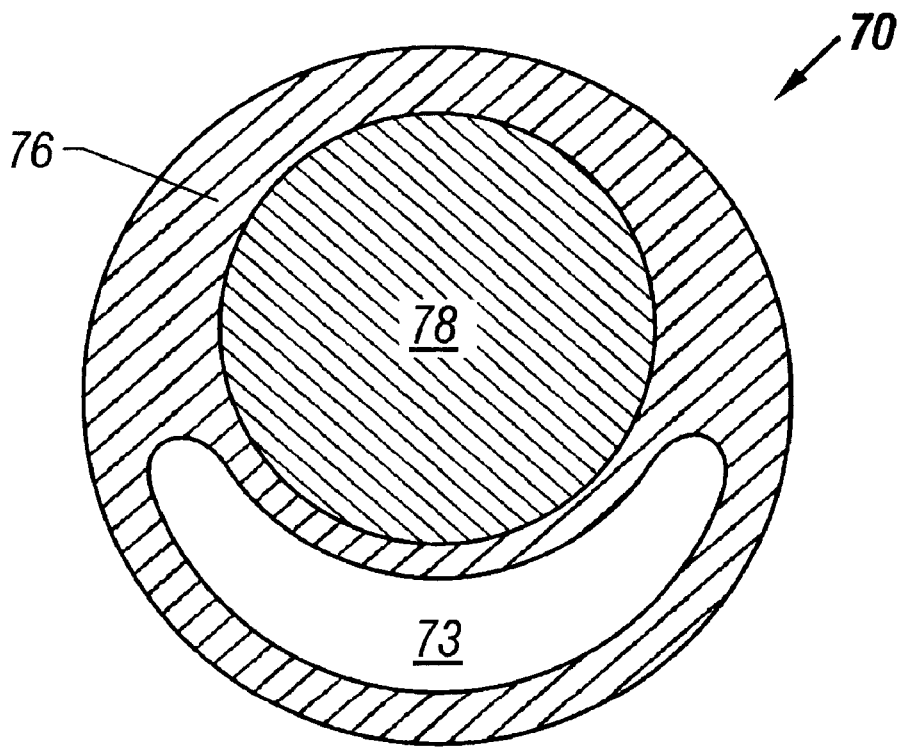
FIG. 7A is a proximal cross-sectional view of a guide wire of the present invention having a dual lumen extension.
Figure 7B:
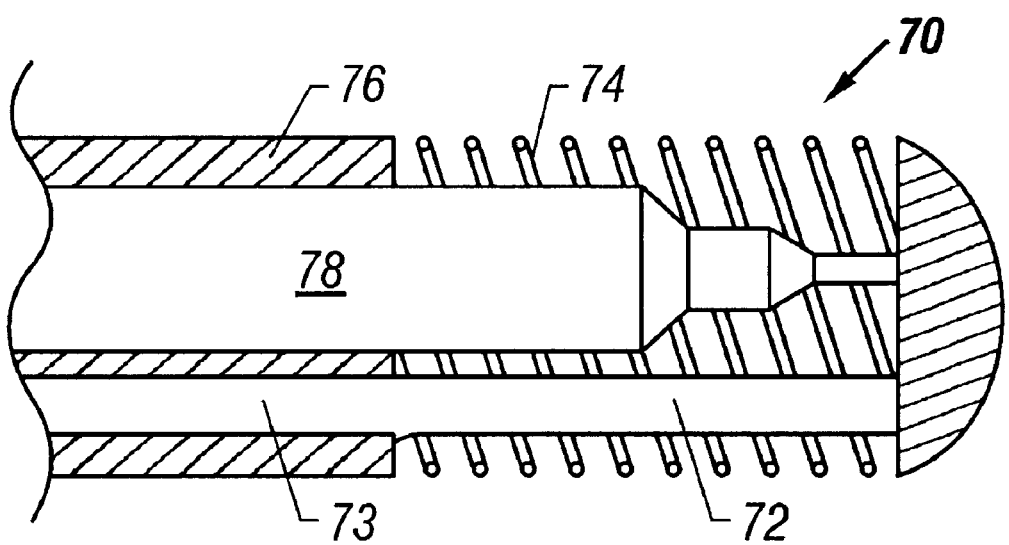
FIG. 7B is a side cross-sectional view of the guidewire illustrated in FIG. 7A.

Another alternative to the fabrication of a guide wire of the present invention is illustrated in FIGS. 7A and 7B. FIG. 7A is a proximal cross-sectional view and FIG. 7B is a side cross-sectional view of a guide wire 70 of the present invention having a dual lumen extension. One lumen encases the core wire 78 while a second lumen 73 serves as the passage for the fluid medium (effectively replacing the balloon stem). Lumen 73 is in fluid communication with balloon 72. Balloon 72 may be glued to shaft 76, or attached using any other appropriate means. The exterior shaft 76 of the guide wire 70 may be extruded directly over the core member 78. The plastic material may then be removed (e.g., ground) to expose the core 78 to function as the distal core.

Figure 8A:
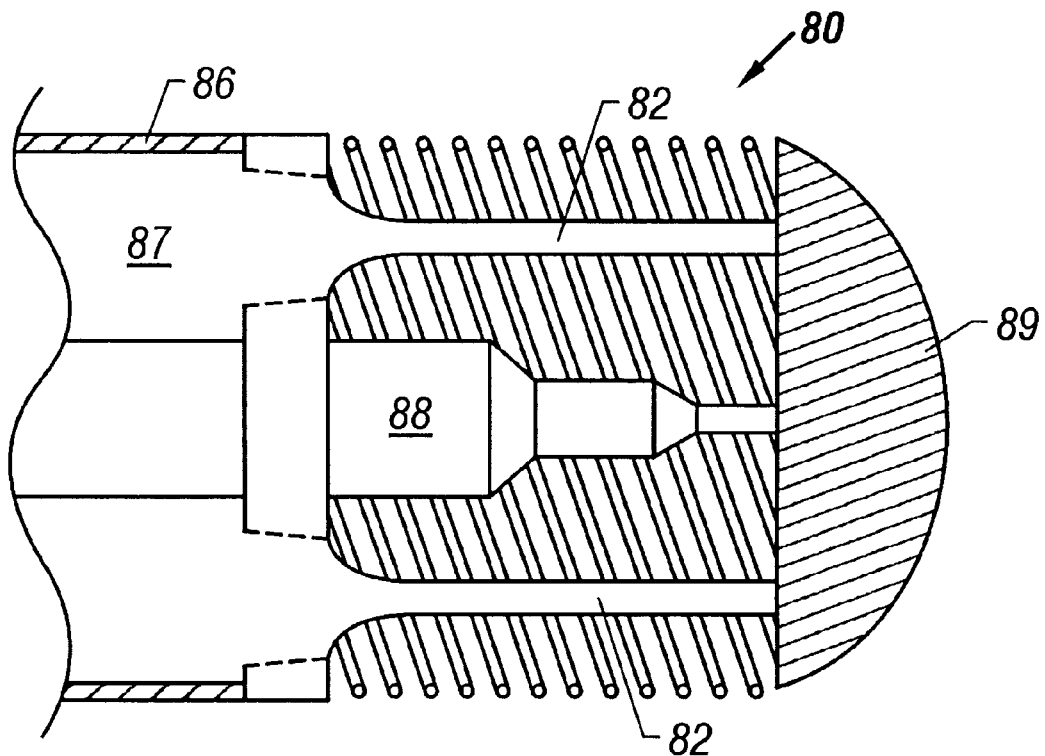
FIG. 8A is a side cross-sectional view of a guide wire of the present invention wherein the lumen itself delivers the fluid medium to the balloon.
Figure 8B:
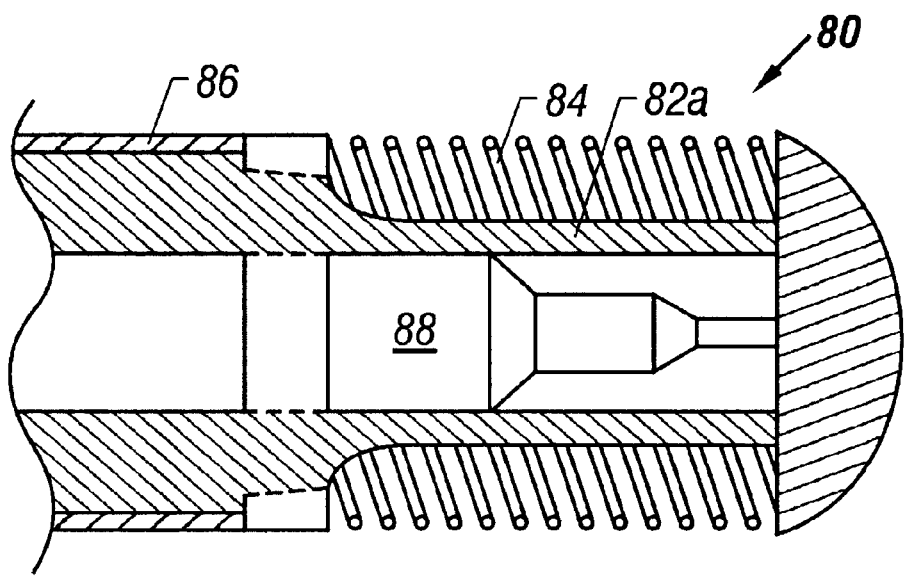
FIG. 8B is a side cross-sectional view of a guidewire such as the one illustrated in FIG. 8A wherein the balloon surrounds the core.

Another alternative to the fabrication of a guide wire of the present invention is illustrated in FIGS. 8A and 8B. FIG. 8A is a side cross-sectional view of a guide wire 80 of the present invention wherein lumen 87 of shaft 86 itself delivers the fluid medium to the balloons 82 located at the distal tip 89 of the guide wire 80. In other words, there is no shaft extending through the lumen 86 to function as a balloon stem. The core element 88 extends through the lumen 87. At least one balloon 82 is disposed substantially parallel to the core 88 and is glued or otherwise attached to the shaft 86 so as to be in fluid communication with lumen 87. Both the core 88 and balloon(s) 82 are encompassed by the coils 84. An inflation device (not shown) is coupled to the lumen 86 to exert pressure via a fluid medium. The fluid medium may then flow through the lumen 87 and into the balloon(s) 82 as needed. For one embodiment, each balloon is in fluid communication with lumen 87. For alternative embodiments, each balloon is in fluid communication with a separate lumen 87 formed in shaft 86.

Figure 8C:
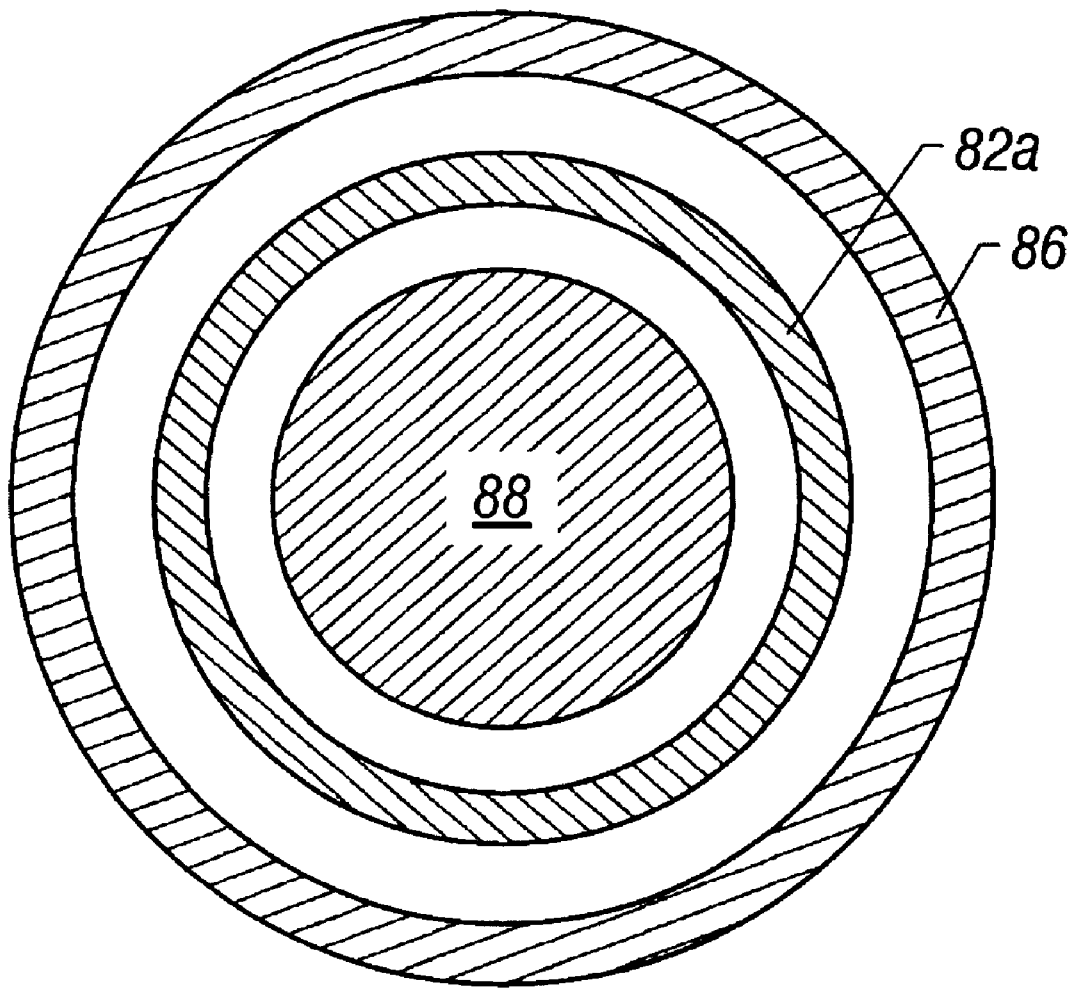
FIG. 8C is a proximal cross-sectional view of the guide wire illustrated in FIG. 8B.

FIG. 8B is a side cross-sectional view of a second guidewire 80 of the present invention wherein the lumen 87 delivers the fluid medium to the balloon 82a. The core element 88 extends through the lumen 87, but in this embodiment is surrounded by the balloon 82a. A proximal cross-sectional view is illustrated in FIG. 8C. The balloon 82a has a donut shape cross-section that completely surrounds the core element 88. Both the balloon 82a and the encompassed core 88 are then surrounded by the coils 84.

Figure 9A:
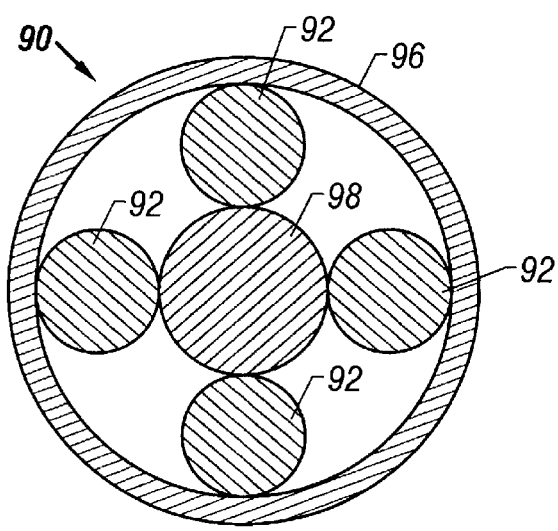
FIG. 9A is a proximal cross-sectional view of an embodiment of the present invention having multiple balloons positioned at equi-distances around the core.
Figure 9B:
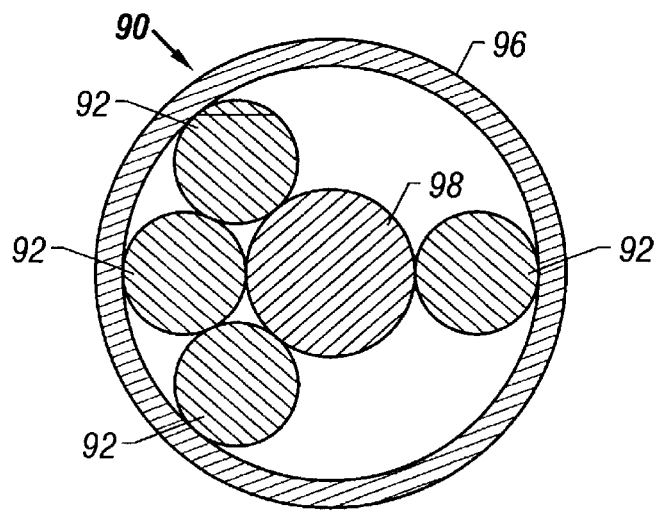
FIG. 9B is a proximal cross-sectional view of an embodiment of the present invention having multiple balloons positioned at non-equidistances around the core.

The number of balloons, the cross-sectional shape of the balloons, and the placement of the balloons within the lumen of the support shaft is a design choice depending primarily on size restraints, the degree of control desired over the flexibility and shape of the guide wire, and the desired ultimate shape of the guide wire. For example, FIG. 9A illustrates a cross-sectional front view of a guide wire of the present invention having four circular balloons 92 surrounding the core 98 of the guide wire 90 and contained within the lumen 96. Independent control over the pressure within each balloon would allow the operator to "bend" the guide wire 90 in all directions. For example, by inflating only the far left balloon 92, the guide wire 90 would bend to the right. Whereas, by inflating both the far left and bottom balloons 92, the guide wire would bend back (into the page) and to the right. This versatility provides the cardiologist with a great deal of control over the positioning of the guide wire 90 when attempting to negotiate an often tortuous and circuitous route to the stenotic site. Note also that the present invention is not limited to the use of four balloons, more or less may be used. Likewise, the positioning of multiple balloons around a core does not have to be at specific equi-distances to one another. For example, the balloons could all be clumped together on one side or several clumped together on one side with merely one on an opposite side (see FIG. 9B). Any of the guide wire assemblies disclosed herein can be modified to use multiple balloons.

Figure 10:
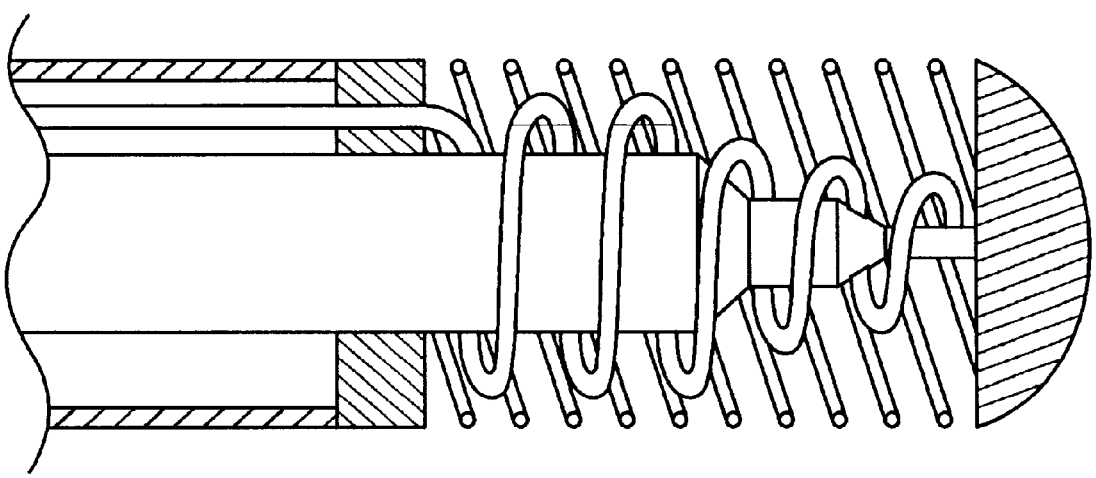
FIG. 10 is a side cross-sectional view of the present invention utilizing a spiral shaped balloon.

Further, the shape of the balloons is not limited to relatively straight tube-like balloons. For example, a spiral shaped balloon (see FIG. 10) or a banana shaped balloon could be used rather than a cylindrical balloon. Each of these shaped balloons would naturally assume their specified shape once inflated. The shape of the balloons could be determined in the molding process. For example, when the balloon is made more elastic on one side a banana shaped balloon may result. Shaped balloons may result in a different "reaction" once inflated as compared to the straight cylindrical balloon. For example, a spiral balloon may stiffen without straightening. This would allow a guidewire in a tortuous path to remain curved, but still become stiffer and hence more supportive. In essence, the curve becomes "locked" into place.

Another possible alternative embodiment of the present invention involves further modification of the traditional guide wires and is illustrated in FIGS. 11A, 11B-1, 11B-2 and 11C. This embodiment consists of a support shaft or housing 116 (e.g., a hypotube) with at least one balloon extending at least partially through lumen 117. The embodiment has several advantages in that coils may not be needed and the core may be eliminated. Instead, the balloon itself can provide the backbone for the hypotube. Further, by eliminating the core, there is room for a larger diameter balloon to be housed within the hypotube lumen. This embodiment allows a hollow tube with use of a balloon to perform as a guide wire that is controllable both in terms of stiffness and/or orientation/position.

Figure 11A:
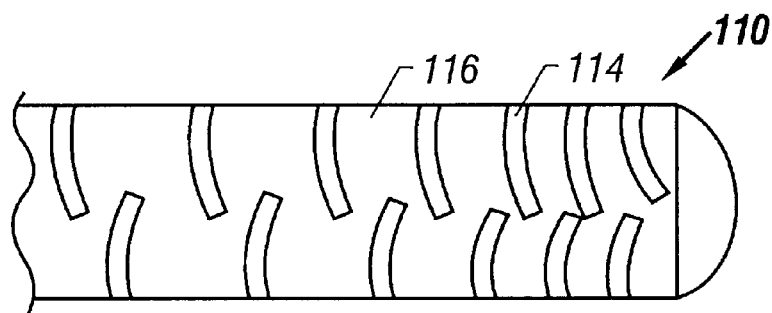
FIG. 11A is a side view of an embodiment of the present invention wherein the guide wire does not possess a core or coils.

FIG. 11A is a side view of the alternative embodiment of the guide wire of the present invention described above. A shaft 116 provides the body of the guide wire 110. Slots 114 in the distal end section of the shaft 116 allow for the shaft 116 to be flexible. The slots 114 may be etched into the shaft 116 with any suitable metal etch technique including a laser etch, saw, and the like. The placement of the slots 114 may be positioned such that the distance between each slot becomes less as the length (L) of the shaft 116 is traversed toward the distal tip 119. The spacing of the slots 114 in this manner will allow for a greater degree of flexibility at the distal tip 119 and a more moderate degree of flexibility on the intermediate section of the shaft 116.

Figures 1, 11B:
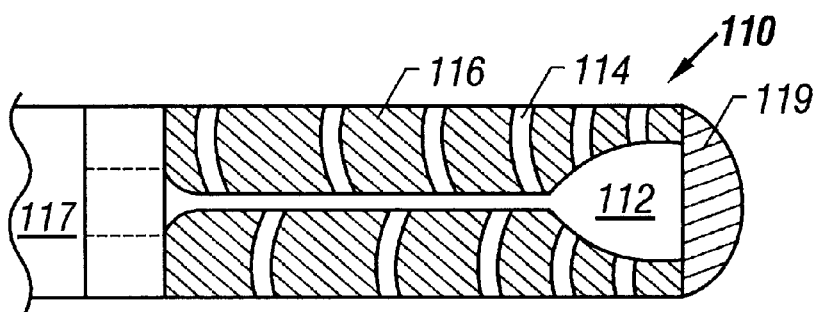
Figures 2, 11B:
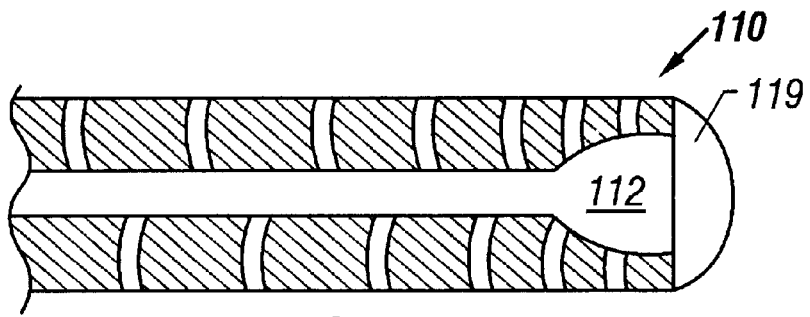
Figure 11C:
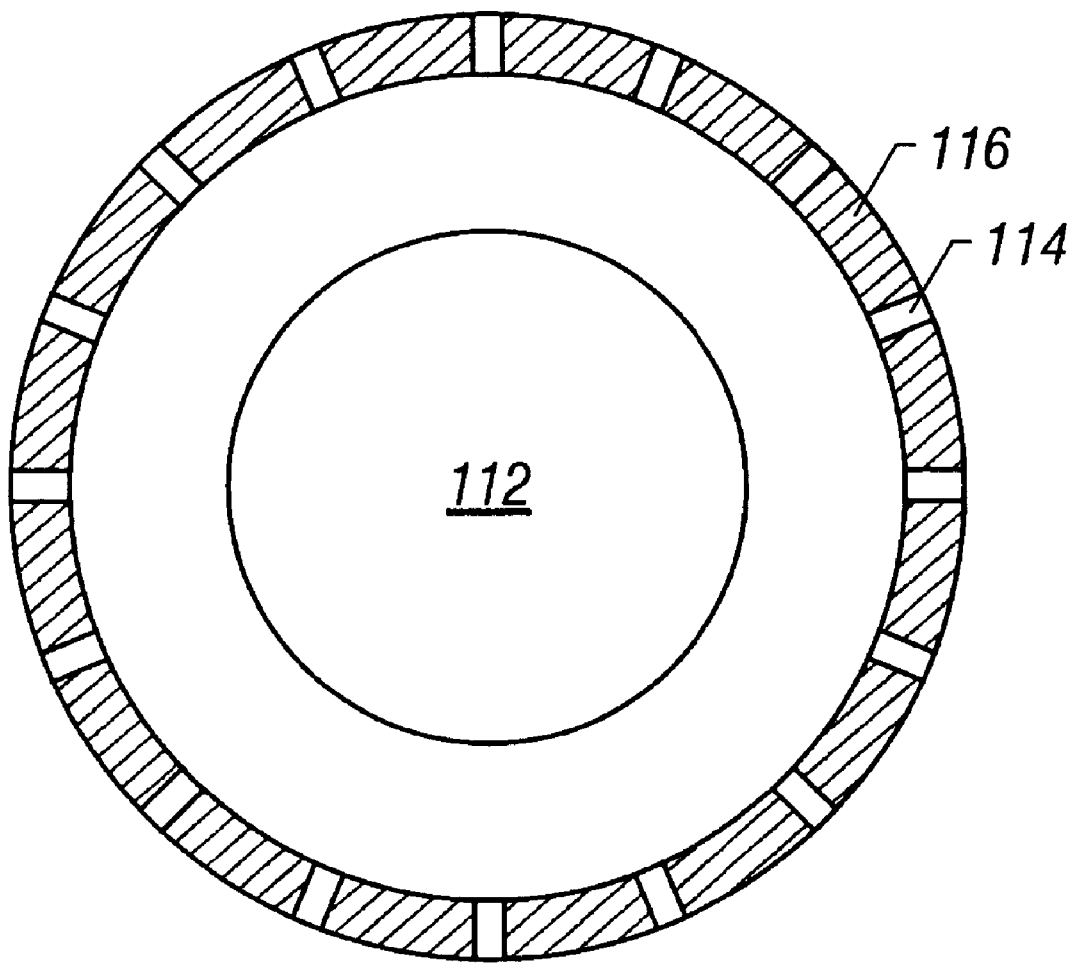
FIG. 11C is a proximal cross-sectional view of the guide wire illustrated in 11 B-1.

FIGS. 11B-1 and 11B-2 are side cross-sectional views of two possible configurations of the balloon 112 encased within lumen 117 of shaft 116. In FIG. 11B-1, the balloon 112 does not extend through the entire length of the shaft 116. Instead the balloon 112 extends through the distal slotted section of shaft 116 and is then affixed to the interior sides of the shaft 116. (Alternatively, a seal or cap could separate the slotted and unslotted sections of the shaft 116 and the balloon 112 could be affixed to an opening in the seal or cap.) In this configuration, the lumen 117 of the shaft 116 would deliver the fluid medium to the balloon 112 to increase the pressure of the balloon 112 and allow the balloon 112 to vary the stiffness and/or position/orientation of the shaft 116 functioning as the guide wire 110. FIG. 11C illustrates a proximal cross-sectional view of the guide wire illustrated in FIG. 11B-1. FIG. 11B-2 illustrates a modification of the balloon 112. In this configuration, the balloon 112 extends the full length of the shaft 116 and is coupled to the inflation device itself (not shown). In configuration 11B-2, the shaft 116 could be a coil wound from flat ribbon material, round material, or round material that is then ground. In other words, the shaft 116 is not limited to a tube.

The slotted guide wire design illustrated in FIGS. 11A–11C could also be used with shape memory alloy actuators in addition to or in place of the balloon 112. Further, with each configuration, the slotted hypotube guide wire could be coated with a material to make it radiopaque.

Figure 12:
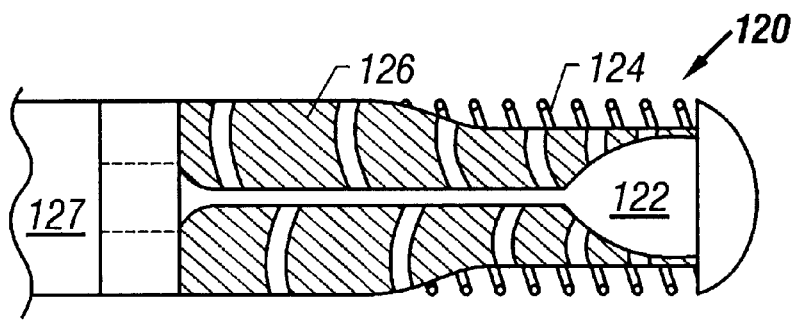
FIG. 12 is a side cross-sectional view of a guide wire having a coil formed over the distal end of a graded shaft.

FIG. 12 is a side cross-sectional illustration of a guide wire 120 having a graded shaft 126 in which there is a coil 124 formed over the distal end of the graded shaft. A balloon 122 within the lumen 127 of the shaft 126 still provides the means of stiffening and/or repositioning the shaft 126.

Various methods of inflating the balloons described in the above embodiments may be used. In the preferred embodiment, an inflation device is coupled to the proximal end of the balloon (i.e., the control end located outside the patient's body.) The inflation device delivers a fluid medium to the balloon to increase the internal pressure of the balloon and stiffen and/or change the shape or orientation of the balloon. Any type of fluid medium may be used. Preferably, a fluid medium is chosen that will not harm the patient if there is an unavoidable leak. For this reason, a saline solution is often preferred. An added benefit to inflating the balloons through use of a fluid medium is that the fluid medium used could be radiopaque. The radiopaque characteristic of the fluid medium would allow the cardiologist through use of a fluoroscope to observe when the balloon is inflated, helping him track both the location and orientation/shape of the guide wire. Note also that the balloon material itself may be radiopaque.

The guide wires described in the present invention may be comprised of the same basic materials and may be fabricated using the same basic methods used to construct guide wires heretofore used. The balloons (including both the approximately constant diameter balloon and the balloon stem having a larger balloon diameter located at its distal end) may be made from a variety of materials. In the preferred embodiment, polyethylene terephthalate (PET) is used primarily due to its ease of use in accurately determining and constructing an appropriate and consistent balloon wall thickness. Other materials that could also be used include any materials used for balloon angioplasty catheters, including nylons, polyethylene, other polyesters, or any other kind of formable plastic material. When using the balloon stem having a balloon at its distal end, the balloon may be comprised of any of the above-mentioned materials, but also may be comprised of polyurethane or polyether block amides (PEBAX). In general, the type of material used for the balloons is a design decision typically governed by the amount of variation the balloon will undergo with respect to both size, position, stiffness, and rigidity. Additionally, either or both of the balloon and balloon stem could be inflated with contrast radiopacity such that each could be seen under a fluoroscope.

As discussed above with respect to FIG. 1, the balloon and balloon stem can be a single piece having a substantially constant diameter with no distinction between the two parts. In other words, a polymer tube could function for the whole piece. The single piece balloon stem/balloon could also have a non-linear diameter for a portion of the piece with a bulb on the distal end. The balloon and balloon stem may also be comprised of separate parts joined together. If separate parts, the balloon and balloon stem may be joined by glue. Plastic welding, fusion, induction, ultrasonic, etc. Typically, in this embodiment the balloon stem provides a more rigid shaft while the balloon is more flexible.

The coils of the present invention may be comprised of any coils currently being used. In one embodiment, the distal coil section is approximately 2–30 cm long. The coil joints are typically formed with a "glue" (i.e., a polymer adhesive). However, solder could be used at the coil joints if the plastic pieces of the guide wire were protected. Further, the coil may consist of a radiopaque tip coil and an intermediate coil or a single radiopaque stretch of coil.

The present invention provides several advantages over guide wires currently used in the art. First, the present invention eliminates the need for the use of two guide wires in a procedure—one having a floppy distal end for insertion and direction through the arterial branch and a second having a stiff body length and/or distal end for delivery of the catheter to the stenotic site. Instead, the present invention provides a single guide wire able to initially enter the body and maze of arterial branches in a flexible or floppy state. The same guide wire can later be bent or otherwise re-oriented while still in the body in order to negotiate the often circuitous path required to reach the stenotic site, and/or can be made stiffer to provide the required pushability characteristic. Second, the present invention is approximately the same size as a conventional guide wire. Size constraints have heretofore often impeded the use of prior art guide wire devices making use of multiple wires and/or pulleys to manipulate the distal tip of the guide wire. Such prior art devices have also been unsuccessful achieving precise control over long distances, thus dictating a constraint on the length of the guide wire. Third, the present invention provides a more immediate response time when stiffening the distal tip of the guide wire than previous designs, such as those utilizing shape memory alloy devices. Thus, the present invention comprises an improved method and apparatus that provides a readily insertable guide wire that is also accurately steerable and provides for reorientation of the distal tip of the guide wire as needed.

We claim:

1. A guide wire assembly comprising:
   a guide wire shaft having a lumen;
   a core member housed within said lumen; and,
   at least one balloon housed within said lumen, said balloon within said shaft, said balloon having a variable shape and a variable internal pressure.

2. The assembly of claim 1 wherein as said internal pressure within said balloon increases said balloon becomes relatively stiff.

3. The assembly of claim 1 wherein said balloon has a first shape at a first internal pressure and as said internal pressure within said balloon increases said balloon acquires a second shape different from said first shape.

4. The assembly of claim 3 wherein said first shape is an extreme J-shape and said second shape is a standard J-shape.

5. The assembly of claim 3 wherein said shape is a J-shape and said second shape is substantially straight.

6. The assembly of claim 1 further comprising a plurality of said balloons.

7. The assembly of claim 6 wherein said plurality of said balloons are positioned around said core member.

8. The assembly of claim 7 wherein said plurality of said balloons are positioned around said core member at equidistances apart.

9. The assembly of claim 6 wherein said internal pressure within at least one of said plurality of said balloons increases such that said at least one of said plurality of said balloons becomes relatively stiff.

10. The assembly of claim 6 wherein at least one of said plurality of said balloons has a first shape at a first internal pressure and said internal pressure within at least one of said plurality of said balloons increases such that said at least one of said plurality of said balloons acquires a second shape different from said first shape.

11. The assembly of claim 1 wherein said shape of said balloon is a non-linear shape.

12. The assembly of claim 11 wherein said shape of said balloon is a spiral shape such that said balloon circles around said core member.

13. The assembly of claim 1 wherein said shape of said balloon has a cylindrical cross-section.

14. The assembly of claim 13 wherein said cylindrical cross-section has a substantially constant diameter.

15. The assembly of claim 1 wherein said balloon is comprised of a balloon stem having a bulb at a distal end of said balloon stem.

16. The assembly of claim 1 wherein said balloon is comprised of a material selected from a group comprising polyethylene terephthalate, (PET), other polyesters, polyurethane, nylon, formable plastic materials, PEBAX, and any material used for balloon angioplasty catheters.

17. The assembly of claim 1 further comprising a pressure transducer for delivering a fluid medium to said balloon such that said internal pressure within said balloon increases.

18. The assembly of claim 1 wherein said balloon surrounds said core member.

19. The assembly of claim 1 wherein said balloon partially surrounds said core member.

20. The assembly of claim 1 further comprising coils surrounding the distal section of said core member and said balloon.

21. A guide wire assembly comprising:
    a shaft having a lumen;
    a core member housed within said lumen and extending therefrom;
    a coil surrounding a portion of said core member extending from said shaft; and,
    at least one balloon coupled to said shaft and disposed between said core and said coil, said balloon being inflatable between said core and said coil, said balloon in fluid communication with said lumen, said balloon having a variable shape and a variable internal pressure.

22. The assembly of claim 21 wherein a fluid medium is delivered to said balloon through said lumen to increase said internal pressure.

23. The assembly of claim 22 wherein as said internal pressure within said balloon increases said balloon becomes relatively stiff.

24. The assembly of claim 22 wherein said balloon has a first shape at a first internal pressure and as said internal pressure within said balloon increases said balloon acquires a second shape different from said first shape.

25. A guide wire assembly comprising:
    a shaft having a first and a second lumen, said second lumen for carrying a fluid medium such that said second lumen has an internal pressure and a first shape wherein said fluid medium is increased in said second lumen such that said second lumen becomes stiff; and,
    a core member housed within said first lumen.

26. The assembly of claim 25 wherein said fluid medium in said second lumen is housed within a balloon.

27. The assembly of claim 25 wherein said fluid medium in said second lumen is increased such that said second lumen acquires a shape different from said first shape.

28. A guide wire assembly comprising:

a guide wire shaft having a lumen; and, at least one balloon housed within said lumen, said balloon inflatable within said shaft, said balloon having a variable shape to bend said guidewire shaft, and a variable internal pressure.

29. The assembly of claim 28, further comprising a plurality of slots in said shaft such that said shaft is flexible.

30. The assembly of claim 29 wherein said slots start at an intermediate point on said shaft and are positioned closer together on said shaft as said slots approach the distal tip of said shaft.

31. The assembly of claim 28 wherein as said internal pressure within said balloon increases said balloon becomes relatively stiff.

32. The assembly of claim 28 wherein as said internal pressure within said balloon increases said balloon changes its shape to bend said shaft.

33. An assembly for use as a guide wire, said guide wire having a stiffness, comprising:

a shaft having a lumen;

a core member housed within said lumen; and, means for altering said stiffness of said guide wire wherein said means for altering stiffness comprises inflating at least one balloon with a fluid medium, said balloon having a variable shape and a variable internal pressure.

34. An assembly for use as a guide wire, said guide wire having an orientation, comprising:

a shaft having a lumen;

a core member housed within said lumen; and, means for altering said orientation of said guide wire wherein said means for altering orientation comprises inflating at least one balloon with a fluid medium, said balloon having a variable shape and a variable internal pressure.

35. The assembly of claim 34 wherein said guide wire is substantially bent when said balloon is deflated and substantially straight when said balloon is inflated.

36. The assembly of claim 34 wherein said guide wire is substantially bent when said balloon is inflated and substantially straight when said balloon is deflated.

37. A method of operating a guide wire comprising:

inserting said guide wire transluminally, said guide wire housing a balloon with an internal pressure; and, altering said internal pressure within said balloon to control the stiffness of at least a portion of the guide wire while said balloon is within said guidewire housing.

38. The method of claim 37, wherein said altering said internal pressure comprises delivering a fluid medium to said balloon.

39. The method of claim 37, wherein altering said internal pressure comprises withdrawing a fluid medium from with said balloon.

40. A method of operating a guide wire comprising:

inserting said guide wire transluminally, said guide wire housing within the shaft at least one balloon with a variable internal pressure; and, altering said internal pressure within said balloon to control the shape of at least a portion of the guide wire.

41. The method of claim 40 wherein said altering comprises delivering a fluid medium to said balloon.

42. The method of claim 40 wherein said altering comprises withdrawing a fluid medium from with said balloon.

43. The method of claim 40 wherein the altering comprises increasing said internal pressure within said balloon such that said guide wire becomes substantially bent.

44. The method of claim 40 wherein said altering comprises increasing the internal pressure such that said guide wire becomes substantially straight.

45. A method for treating a patient comprising:

inserting a guidewire assembly into the body of a patient wherein the guidewire assembly comprises a shaft, lumen, core member and at least one variable shape balloon contained inside said assembly; and, introducing an inflation medium to at least one of the balloons;

changing the shape of at least one of the balloons while it is housed within said assembly by varying the internal pressure of the inflation medium;

inflating and deflating at least one of the balloons to maneuver the guidewire within the body;

guiding the assembly to the desired location within the body;

inflating and deflating at least one of the balloons to change the position of the guidewire;

administering treatment to the body site; and, inflating and deflating at least one of the balloons to move the guidewire assembly.

46. The method of claim 45 wherein the method comprises angioplasty.

* * * * *

UNITED STATES PATENT AND TRADEMARK OFFICE
CERTIFICATE OF CORRECTION

PATENT NO. : 6,146,339
DATED : November 14, 2000
INVENTOR(S) : Biagtan et al.

It is certified that error appears in the above-identified patent and that said Letters Patent is hereby corrected as shown below:

Column 12,
Line 7, after "within" insert -- said --.

Signed and Sealed this

Twenty-sixth Day of July, 2005

JON W. DUDAS
*Director of the United States Patent and Trademark Office*